United States Patent
Derici et al.

(10) Patent No.: US 7,459,417 B2
(45) Date of Patent: Dec. 2, 2008

(54) HAIR CONDITIONING COMPOSITION COMPRISING A SILICONE OIL AND A POLOXAMER OR POLOXAMINE BLOCK COPOLYMER

(75) Inventors: Leo Derici, Wirral (GB); Paul David Jenkins, Wirral (GB); Andrew Malcolm Murray, Wirral (GB); Neil Scott Shaw, Wirral (GB)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 155 days.

(21) Appl. No.: 10/514,218

(22) PCT Filed: Apr. 23, 2003

(86) PCT No.: PCT/EP03/04238

§ 371 (c)(1),
(2), (4) Date: Nov. 10, 2004

(87) PCT Pub. No.: WO03/094873

PCT Pub. Date: Nov. 20, 2003

(65) Prior Publication Data

US 2006/0058204 A1    Mar. 16, 2006

(30) Foreign Application Priority Data

May 10, 2002    (GB) ................... 0210791.0
Dec. 11, 2002    (GB) ................... 0228879.3

(51) Int. Cl.
C11D 9/36    (2006.01)
C11D 1/722   (2006.01)

(52) U.S. Cl. .................. 510/122; 510/119; 510/130; 510/153; 510/181; 510/182; 510/417; 510/421; 510/466; 510/499

(58) Field of Classification Search .............. 510/119, 510/122, 130, 153, 181, 182, 417, 421, 466, 510/499
See application file for complete search history.

(56) References Cited

U.S. PATENT DOCUMENTS

| | | | |
|---|---|---|---|
| 3,753,916 A | 8/1973 | Parran, Jr. | |
| 4,183,917 A * | 1/1980 | Iwao et al. | 424/70.11 |
| 5,100,657 A | 3/1992 | Asher-Jackson et al. | |
| 5,589,177 A * | 12/1996 | Herb et al. | 424/401 |
| 5,641,480 A | 6/1997 | Vermeer | 424/70.24 |
| 5,648,323 A | 7/1997 | Coffindaffer et al. | 510/122 |
| 5,662,892 A | 9/1997 | Bolich, Jr. et al. | |
| 5,709,847 A * | 1/1998 | Bissett et al. | 424/59 |
| 5,733,536 A * | 3/1998 | Hill et al. | 424/70.12 |
| 5,837,661 A | 11/1998 | Evans et al. | 510/122 |
| 5,942,216 A | 8/1999 | Herb et al. | |
| 5,942,479 A | 8/1999 | Frankenbach et al. | 510/159 |
| 5,968,286 A | 10/1999 | Crudele et al. | |
| 5,985,295 A | 11/1999 | Peffly | |
| 6,017,860 A | 1/2000 | Sajic et al. | |
| 6,030,630 A | 2/2000 | Fleury et al. | |
| 6,056,946 A | 5/2000 | Crudele et al. | |
| 6,150,313 A | 11/2000 | Harmalker et al. | |
| 2001/0027171 A1 | 10/2001 | Sajac et al. | |
| 2003/0138465 A9 | 7/2003 | Douin et al. | 424/401 |

FOREIGN PATENT DOCUMENTS

| | | |
|---|---|---|
| EP | 0 715 842 A2 | 6/1996 |
| WO | 92/14440 | 9/1992 |
| WO | 96/17590 | 6/1996 |
| WO | 96/17592 | 6/1996 |
| WO | 97/14405 | 4/1997 |
| WO | 98/50005 | 11/1998 |
| WO | 00/51550 | 9/2000 |

OTHER PUBLICATIONS

Search Report under Section 17 application No. GB 0228879.3 dated May 9, 2003.
Search Report under Section 17 application No. GB 0210791.0 dated Jan. 22, 2003.
International Search Report application No. PCT/EP 03/04237 mailed Sep. 15, 2003.
Co-pending applications Applicant: Derici et al., U.S. Appl. No. 10/514,218, filed Nov. 10, 2004, For: Hair Conditioning Compositions.
Co-pending application Applicant: Derici et al., U.S. Appl. No. 10/514,217, filed Nov. 10, 2004, For: Conditioning Shampoo Composition.
GB Search Report in GB application GB 0228880.1.
KPSS, Kao Professional Salon Service GmbH opposition against EP 1505949 (U.S. Appl. No. 10/514,217)—Nov. 7, 2008.

* cited by examiner

Primary Examiner—Charles I Boyer
(74) Attorney, Agent, or Firm—Karen E. Klumas

(57) ABSTRACT

An aqueous hair conditioner composition comprising: a) a cationic conditioning surfactant, b) discrete, dispersed droplets comprising a water-insoluble conditioning oil and c) a block copolymer with a mean molecular weight of 1000 unified atomic mass units or more, comprising polyethyleneoxide and polypropyleneoxide blocks selected from the group consisting of (i) poloxamers according to formula (I), wherein the mean value of (y) is from 18 to 60 and the mean value (x) is from 7 to 140 such that the mean value of the ratio (x/y) is from 0.4 to 3.0 and (ii) poloxamines according to formula (II), wherein the mean value of (a) is 2 or more and the mean value of (b) is 2 or more.

15 Claims, No Drawings

HAIR CONDITIONING COMPOSITION COMPRISING A SILICONE OIL AND A POLOXAMER OR POLOXAMINE BLOCK COPOLYMER

TECHNICAL FIELD

The invention is concerned with hair-conditioning compositions. It is particularly concerned with hair conditioner compositions, which are applied to the hair after washing or shampooing and subsequent rinsing. More specifically, it is concerned with improving the deposition of conditioning oil onto the tip region of hair, from hair conditioner compositions which contain dispersed hydrophobic conditioning oil droplets.

BACKGROUND AND PRIOR ART

Hair conditioner compositions which provide conditioning to the hair are well known in the art. Such compositions comprise one or more conditioning agents. The purpose of the conditioning agent is to make the hair easier to comb when wet and more manageable when dry, e.g. less static and flyaway. They also make the hair feel softer. Typically, these conditioning agents are either water-insoluble oily materials which act by spreading on the hair in the form of a film, or cationic surfactant materials or polymers, which adsorb onto the hair surface.

Hair conditioners can be in the form of rinse-off conditioners (usually applied to the hair after shampooing as a liquid or mousse) or leave-on products such as hair oils or serums, mousses and styling products.

Typically, water-insoluble oily conditioning materials are dispersed in aqueous products in the form of small droplets or particles in order to facilitate the stability of the dispersion to phase separation and to enhance the deposition of the oily material onto the hair.

A preferred water-insoluble oily conditioning material is based on silicone polymers, preferably polydimethylsiloxanes, with or without various functionalising groups. Non-silicone conditioning oils include hydrocarbon oils and triglycerides.

Although these cationic surfactants, cationic polymers and water-insoluble oily conditioning materials provide conditioning effects to the hair, it is desirable to improve the conditioning effects obtainable from them.

Natural oils secreted by the sebaceous gland at the base of the hair lead to hair being more hydrophobic near the root rather than near the tip. This means that droplets of hydrophobic conditioning oil deposited onto hair are more likely to spread and form films on the hair at the base of the hair rather than near the tip of the hair, and this is found in practice.

Certain consumers find the effects arising from this effect to be undesirable in that it may lead to the hair feeling greasy at the roots or heavy and dull.

In attempts to overcome the problems in the prior art, it has been considered desirable to target the deposition of the conditioning oil droplets onto the tip regions of the hair in preference to the basal regions, and much research has been carried out in this field of work. Although it would be desirable to make the surface of the oil droplets more hydrophilic, it had always been considered that the high levels of cationic surfactant in rinse-off hair conditioner compositions would dominate the surface chemistry and hydrophilicity of the oil droplets. Thus the conventional view is that irrespective of any additives added to the conditioning oil droplets, the conditioning surfactant would control the droplet hydrophilicity and deposition.

It has now surprisingly been found, that by blending certain types of surface active block copolymers of a high molecular weight with conditioning oil emulsion droplets, enhanced deposition of the droplets onto the tip regions of hairs can be achieved. Although not wishing to be bound by the scientific reasoning underlying this phenomenon, it seems that surface active polymer remains at the droplet surface, even in the presence of other surfactant molecules from the conditioner, making the droplets more hydrophilic than the droplets in conventional oil droplet-containing hair conditioner compositions. This leads to improved deposition of the droplets towards the more hydrophilic tip region of the hair.

The present invention concerns the use of Poloxamers (CTFA designation) to enhance the deposition of hydrophobic conditioning oil onto the hair tip region from hair conditioner compositions, particularly from rinse-off conditioner compositions.

U.S. Pat. No. 3,753,916 discloses the use of cationic polymers as deposition aids for conditioning oils. Poloxamers are mentioned under the trade name Pluronic as optional ingredients.

WO 92/14440 discloses Pluronics (Poloxamers) in anti-dandruff shampoos as one of a class of 'synergisers' that unexpectedly enhance anti-dandruff efficacy.

WO 96/17590 discloses personal washing compositions containing lipids as the conditioning phase. The lipids are emulsified with a nonionic emulsifier. Poloxamers are listed as one of the possible polyalkoxy nonionic emulsifiers with HLB (hydrophile lipophile balance) in the range 1 to 15.

U.S. Pat. No. 5,100,657 lists Pluronics (Poloxamers) as optional ingredients in hair conditioner compositions.

SUMMARY OF THE INVENTION

In a first aspect, the invention provides an aqueous hair conditioner composition comprising:
a) a cationic conditioning surfactant,
b) discrete, dispersed droplets comprising a water insoluble conditioning oil and
c) a block copolymer with a mean molecular weight of 1000 unified atomic mass units or more, comprising polyethyleneoxide and polypropyleneoxide blocks selected from the group consisting of (i) poloxamers according to formula I:

I:

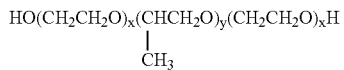

wherein the mean value of y is from 18 to 60 and the mean value x is from 7 to 140 such that the mean value of the ratio x/y is from 0.4 to 3.0. and (ii) poloxamines according to formula II:

II:

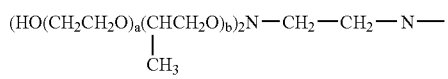

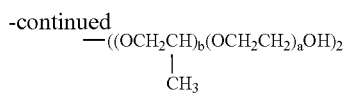

wherein the mean value of a is 2 or more and the mean value of b is 2 or more.

DETAILED DESCRIPTION

Compositions in accordance with the invention are formulated as compositions for applying to the hair and subsequent rinsing such as hair conditioner or conditioner mousse or gel.

By tip region of the hair is meant the distal half of each individual hair.

Surface Active Polymer

An essential component of compositions according to the invention is a surface active block copolymer. This is a block copolymer based on polyethyleneoxide (EO) and polypropyleneoxide (PO) blocks. Suitably, the mean molecular weight of the block copolymer is 1000 unified atomic mass units or more, preferably 2000 or more, more preferably 4000 or more, most preferably 8000 or more.

The mean molecular weight is suitably measured by determining the hydroxyl number for the polymer then transforming this into molecular weight. This corresponds to a number based mean molecular weight.

Suitable EO/PO block copolymers according to formula I have the CTFA designation Poloxamer.

I:

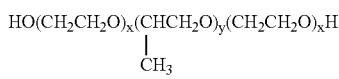

These are commercially available under the trade name "Pluronic" from BASF. Suitably, the mean value of y is from 18 to 60, preferably from 30 to 60. The mean value x is from 7 to 140 such that the ratio x/y is from 0.4 to 3.0, preferably from 1.0 to 2.7.

In formula I, the degree of polymerisation, x, is indicated as the same for each polyethyleneoxide block. For the sake of clarity, it should be explained that these degrees of polymerisation are mean values and are approximately the same rather than identical for any particular formula.

This is a result of the polymerisation methods used for production of the compounds.

Another suitable block copolymer is according to formula II and has the CTFA designation "Poloxamine".

II:

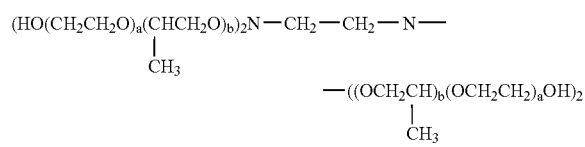

Poloxamines are commercially available from BASF under the trade name "Tetronic". Suitably the mean value of a is 2 or more and the mean value of b is 2 or more.

Preferably, the mean value of a is 3 or more and the mean value of b is 3 or more. It is also preferred if the ratio a/b is from 0.1 to 15, more preferably from 0.5 to 6.

In formula II, the degrees of polymerisation, a and b are indicated as the same for each polyethyleneoxide and polypropylene block respectively. For the sake of clarity, it should be explained that these degrees of polymerisation are mean values and are approximately the same rather than identical for any particular formula. This is a result of the polymerisation methods used for production of the compounds. Suitably, the level of surface active block copolymer is from 0.005% to 5% by weight of the composition, preferably from 0.01% to 2%, more preferably from 0.01% to 0.7%, even more preferably from 0.01% to 0.4%.

Conditioning Oil

An essential component of compositions according to the invention is a hydrophobic conditioning oil. In order for such an oil to exist in discrete droplets in the compositions according to the invention, it must be water-insoluble. By water-insoluble is meant that the solubility in water at 25° C. is 0.01% by weight or less.

It is preferred if the conditioning oil is non-volatile, by which it is meant that the vapour pressure of the oil at 25° C. is less than 10 Pa.

As used herein, the term "conditioning oil" includes any material, which is used to give a particular conditioning benefit to hair. For example, suitable materials are those which deliver one or more benefits relating to shine, softness, combability, wet-handling, anti-static properties, protection against damage, body, volume, stylability and manageability.

Preferred conditioning oils will have a viscosity of less than 5 Pa·s, more preferably less than 1 Pa·s, and most preferably less than 0.5 Pa·s, e.g. 0.1 Pa·s and under as measured at 25° C. at a shear rate of 1 $\text{sec}^{-1}$. Oily and fatty materials with higher viscosities may be used. For example, materials with viscosities as high as 65 P·s may be used.

Suitable hydrophobic conditioning oils are selected from hydrocarbon oils, fatty esters, silicone oils and mixtures thereof.

Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably contain from about 12 to about 30 carbon atoms. Branched chain hydrocarbon oils can and typically may contain higher numbers of carbon atoms. Also suitable are polymeric hydrocarbons of alkenyl monomers, such as $C_2$-$C_6$ alkenyl monomers. These polymers can be straight or branched chain polymers. The straight chain polymers will typically be relatively short in length, having a total number of carbon atoms as described above for straight chain hydrocarbons in general. The branched chain polymers can have substantially higher chain length. The number average molecular weight of such materials can vary widely, but will typically be up to about 2000, preferably from about 200 to about 1000, more preferably from about 300 to about 600.

Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of hexadecane and eicosane, such as 2,2,4,4,6,6,8,8-dimethyl-10-methylundecane and 2,2,4,4,6,6-dimethyl-8-methylnonane, sold by Permethyl Corporation. A further example of a hydrocarbon polymer is polybutene, such as the copolymer of isobutylene and butene. A commercially available material of this type is L-14 polybutene from Amoco Chemical Co. (Chicago, Ill., U.S.A.).

Particularly preferred hydrocarbon oils are the various grades of mineral oils. Mineral oils are clear oily liquids obtained from petroleum oil, from which waxes have been removed, and the more volatile fractions removed by distillation. The fraction distilling between 250° C. to 300° C. is termed mineral oil, and it consists of a mixture of hydrocarbons ranging from $C_{16}H_{34}$ to $C_{21}H_{44}$. Suitable commercially available materials of this type include Sirius M85 and Sirius M125, all available from Silkolene.

Suitable fatty esters are characterised by having at least 10 carbon atoms, and include esters with hydrocarbyl chains derived from fatty acids or alcohols, e.g., monocarboxylic acid esters, polyhydric alcohol esters, and di- and tricarboxylic acid esters. The hydrocarbyl radicals of the fatty esters hereof can also include or have covalently bonded thereto other compatible functionalities, such as amides and alkoxy moieties, such as ethoxy or ether linkages.

Monocarboxylic acid esters include esters of alcohols and/or acids of the formula R'COOR in which R' and R independently denote alkyl or alkenyl radicals and the sum of carbon atoms in R' and R is at least 10, preferably at least 20.

Specific examples include, for example, alkyl and alkenyl esters of fatty acids having aliphatic chains with from about 10 to about 22 carbon atoms, and alkyl and/or alkenyl fatty alcohol carboxylic acid esters having an alkyl and/or alkenyl alcohol-derived aliphatic chain with about 10 to about 22 carbon atoms, benzoate esters of fatty alcohols having from about 12 to 20 carbon atoms.

The monocarboxylic acid ester need not necessarily contain at least one chain with at least 10 carbon atoms, so long as the total number of aliphatic chain carbon atoms is at least 10. Examples include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate. Di- and trialkyl and alkenyl esters of carboxylic acids can also be used. These include, for example, esters of $C_4$-$C_8$ dicarboxylic acids such as $C_1$-$C_{22}$ esters (preferably $C_1$-$C_6$) of succinic acid, glutaric acid, adipic acid, hexanoic acid, heptanoic acid, and octanoic acid. Examples include diisopropyl adipate, diisohexyl adipate, and diisopropyl sebacate. Other specific examples include isocetyl stearoyl stearate, and tristearyl citrate.

Polyhydric alcohol esters include alkylene glycol esters, for example ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol monostearate, ethoxylated propylene glycol monostearate, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, polyoxyethylene sorbitan fatty acid esters and mono-, di-and triglycerides.

Particularly preferred fatty esters are mono-, di- and triglycerides, more specifically the mono-, di-, and tri-esters of glycerol and long chain carboxylic acids such as $C_1$-$C_{22}$ carboxylic acids. A variety of these types of materials can be obtained from vegetable and animal fats and oils, such as coconut oil, castor oil, safflower oil, sunflower oil, cottonseed oil, corn oil, olive oil, cod liver oil, almond oil, avocado oil, palm oil, sesame oil, peanut oil, lanolin and soybean oil. Synthetic oils include triolein and tristearin glyceryl dilaurate.

Specific examples of preferred materials include cocoa butter, palm stearin, sunflower oil, soyabean oil and coconut oil.

The oil may be blended with other materials in the discrete droplets present in compositions according to the invention.

It is preferred that the d (0.5) volume-based median particle diameter of the hydrophobic conditioning oil droplets in the composition is less than 100 micrometers, more preferably less than 40 micrometers, even more preferably less than 10 micrometers and most preferably less than 6 micrometers. Larger particle diameters lead to problems in stabilising the composition from separation of components. Practical difficulties in making emulsion droplets with a median diameter of 0.02 micrometers or less are known to those skilled in the art. Thus it is preferred if the volume-based median diameter d (0.5) is greater than 0.02 micrometers, more preferably greater than 0.03 micrometers, even more preferably greater than 0.1 micrometers. Preferred ranges of median diameter can be formed by combining any of the preferred minimum diameters with any of the preferred maximum diameters. Volume-based median droplet diameter d (0.5) may be measured by means of a laser light scattering technique, for example using a 2600D Particle Sizer from Malvern Instruments.

The total amount of hydrophobic conditioning oil present in the composition is preferably from 0.1% to 10% by weight of the total composition more preferably from 0.2% to 6%, most preferably 0.5% to 4%.

Silicone Conditioning Oils

Preferred hydrophobic conditioning oils for use in compositions according to the invention are silicones.

Suitable silicones for use as conditioning oils include polydiorganosiloxanes, in particular polydimethylsiloxanes which have the CTFA designation dimethicone. Also suitable for use in compositions of the invention are polydimethyl siloxanes having hydroxyl end groups, which have the CTFA designation dimethiconol.

It is preferred if the silicone oil also comprises a functionalised silicone. Suitable functionalised silicones include, for example, amino-, carboxy-, betaine-, quaternary ammonium-, carbohydrate-, hydroxy- and alkoxy-substituted silicones. Preferably, the functionalised silicone contains multiple substitutions.

For the avoidance of doubt, as regards hydroxyl-substituted silicones, a polydimethylsiloxane merely having hydroxyl end groups (which have the CTFA designation dimethiconol) is not considered a functionalised silicone within the present invention. However, a polydimethylsiloxane having hydroxyl substitutions along the polymer chain is considered a functionalised silicone.

Preferred functionalised silicones are amino-functionalised silicones. Suitable amino functionalised silicones are described in EP 455,185 (Helene Curtis) and include trimethylsilylamodimethicone as depicted below, and are sufficiently water insoluble so as to be useful in compositions of the invention:

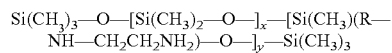

wherein x+y is a number from about 50 to about 500, and the weight percent amine functionality is in the range of from about 0.03% to about 8% by weight of the molecule, and wherein R is an alkylene group having from 2 to 5 carbon atoms. Preferably, the number x+y is in the range of from about 100 to about 300, and the weight percent amine functionality is in the range of from about 0.03% to 8% by weight of the molecule.

As expressed here, the weight percent amine functionality is measured by titrating a sample of the amino-functionalised silicone against alcoholic hydrochloric acid to the bromocresol green end point. The weight percent amine is calculated using a molecular weight of 45 (corresponding to $CH_3$—$CH_2$—$NH_2$).

Suitably, the weight percent amine functionality measured and calculated in this way is in the range from 0.03% to 8%, preferably from 0.5% to 4%.

An example of a commercially available amino-functionalised silicone useful in the silicone component of the composition of the invention is DC-8566 available from Dow Corning (INCI name: dimethyl,methyl (aminoethylaminoisobutyl) siloxane). This has a weight percent amine functionality of about 1.4%.

By "amino functional silicone" is meant a silicone containing at least one primary, secondary or tertiary amine group, or a quaternary ammonium group. Examples of suitable amino functional silicones include: polysiloxanes having the CTFA designation "amodimethicone". Specific examples of amino functional silicones suitable for use in the invention are the aminosilicone oils DC-8220, DC-8166, DC-8466, and DC-8950-114 (all ex Dow Corning), and GE 1149-75, (ex General Electric Silicones). Suitable quaternary silicone polymers are described in EP-A-0 530 974. A preferred quaternary silicone polymer is K3474, ex Goldschmidt.

Another preferred functional silicone for use as a component in the hydrophobic conditioning oil is an alkoxy-substituted silicone. Such molecules are known as silicone copolyols and have one or more polyethyleneoxide or polypropyleneoxide groups bonded to the silicone polymer backbone, optionally through an alkyl linking group.

A non-limiting example of a type of silicone copolyol useful in compositions of the invention has a molecular structure according to the formula depicted below:

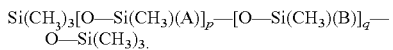

In this formula, A is an alkylene chain with from 1 to 22 carbon atoms, preferably 4 to 18, more preferably 10 to 16. B is a group with the structure: 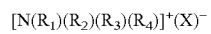—(R)-(EO)$_r$(PO)$_s$—OH wherein R is a linking group, preferably an alkylene group with 1 to 3 carbon atoms. Preferably R is —$(CH_2)_2$—. The mean values of r and s are 5 or more, preferably 10 or more, more preferably 15 or more. It is preferred if the mean values of r and s are 100 or less. In the formula, the value of p is suitably 10 or more, preferably 20 or more, more preferably 50 or more and most preferably 100 or more. The value of q is suitably from 1 to 20 wherein the ratio p/q is preferably 10 or more, more preferably 20 or more. The value of p +q is a number from 11 to 500, preferably from 50 to 300.

Suitable silicone copolyols have an HLB of 10 or less, preferably 7 or less, more preferably 4 or less. A suitable silicone copolyol material is DC5200, known as Lauryl PEG/PPG-18/18 methicone (INCI name), available from Dow Corning.

It is preferred to use a combination of functional and non-functional silicones as the hydrophobic silicone conditioning oil. Preferably the silicones are blended into common droplets prior to incorporation into compositions according to the invention.

The viscosity of the droplets hydrophobic silicone conditioning oil, measured in isolation from the rest of the composition (i.e. not the viscosity of any pre-formed emulsion, but of the hydrophobic conditioning oil itself) is typically from 350 to 200,000,000 mm$^2$sec$^{-1}$ at 25° C. Preferably the viscosity is at least 5,000 mm$^2$sec$^{-1}$ at 25° C., more preferably at least 10,000 mm$^2$sec$^{-1}$. Preferably the viscosity does not exceed 20,000,000 mm$^2$sec$^{-1}$, more preferably 10,000,000 mm$^2$sec$^{-1}$, most preferably 5,000,000 mm$^2$sec$^{-1}$.

Suitable methods for measuring the kinematic viscosity of silicone oils are known to those skilled in the art, e.g. capillary viscometers. For high viscosity silicones, a constant stress rheometer can also be used to measure dynamic viscosity which is related to kinematic viscosity by the density of the silicone. The viscosity should be measured at low shear rates, typically less than 10 s$^{-1}$, such that the silicone exhibits Newtonian behaviour (i.e. viscosity independent of shear rate).

Conditioning Surfactant

Hair conditioner compositions according to the invention comprise one or more conditioning surfactants which are cosmetically acceptable and suitable for topical application to the hair.

Suitable conditioning surfactants are selected from cationic surfactants, used singly or in admixture. Cationic surfactants useful in compositions of the invention contain amino or quaternary ammonium hydrophilic moieties which are positively charged when dissolved in the aqueous composition of the present invention.

Examples of suitable cationic surfactants are those corresponding to the general formula:

$$[N(R_1)(R_2)(R_3)(R_4)]^+(X)^-$$

in which $R_1$, $R_2$, $R_3$, and $R_4$ are independently selected from (a) an aliphatic group of from 1 to 22 carbon atoms, or (b) an aromatic, alkoxy, polyoxyalkylene, alkylamido, hydroxyalkyl, alkoylalkyl, aryl or alkylaryl group having up to 22 carbon atoms; and X is a salt-forming anion such as those selected from halogen, (e.g. chloride, bromide), acetate, citrate, lactate, glycolate, phosphate nitrate, sulphate, and alkyl-sulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

Preferred cationic surfactants for conditioner compositions of the present invention are so-called monoalkyl quaternary ammonium compounds in which $R_1$ has an alkyl chain length from C16 to C22 and $R_2$, $R_3$ and $R_4$ have 2 or less carbon atoms.

Other preferred cationic surfactants are so-called dialkyl quaternary ammonium compounds in which $R_1$ and $R_2$ independently have an alkyl chain lengths from C16 to C22 and $R_3$ and $R_4$ have 2 or less carbon atoms.

Examples of suitable cationic surfactants include quaternary ammonium compounds, particularly trimethyl quaternary compounds.

Preferred quaternary ammonium compounds include cetyltrimethylammonium chloride, behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, PEG-2 oleylammonium chloride and salts of these, where the chloride is replaced by halogen, (e.g., bromide), acetate, citrate, lactate, glycolate, phosphate nitrate, sulphate, or alkylsulphate. Further suitable cationic surfactants include those materials having the CTFA designations Quaternium-5, Quaternium-31 and Quaternium-18. Mixtures of any of the foregoing materials may also be suitable. Particularly useful quaternary ammonium cationic surfactants for use in hair conditioners of the invention are cetyltrimethylammonium chloride, available commercially, for example as GENAMIN CTAC, ex Hoechst Celanese and Arquad 16/29 supplied by Akzo Nobel, and behenyltrimethylammonium chloride (BTAC) such as Genamin KDM-P supplied by Clariant.

Another suitable cationic conditioning surfactant is a dialkoylalkyl dimethylammonium halide. An example of such a compound has the CTFA designation dipalmitoyethyldimethylammonium chloride.

Further suitable cationic systems are primary, secondary, and tertiary fatty amines used in combination with an acid to provide the cationic species. The alkyl groups of such amines preferably have from 12 to 22 carbon atoms, and can be substituted or unsubstituted.

Particularly useful are amido substituted tertiary fatty amines, in particular tertiary amines having one $C_{12}$ to $C_{22}$ alkyl or alkenyl chain. Such amines, useful herein, include stearamidopropyidimethylamine, stearamidopropyidiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide.

Also useful are dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, and arachidyl behenylamine.

As stated previously, these amines are typically used in combination with an acid to provide the cationic species. The preferred acid useful herein includes L-glutamic acid, lactic acid, hydrochloric acid, malic acid, succinic acid, acetic acid, fumaric acid, tartaric acid, citric acid, L-glutamic hydrochloride, and mixtures thereof; more preferably L-glutamic acid, lactic acid, citric acid. Cationic amine surfactants included among those useful in the present invention are disclosed in U.S. Pat. No. 4,275,055 to Nachtigal, et al., issued Jun. 23, 1981.

The molar ratio of protonatable amines to $H^+$ from the acid is preferably from about 1:0.3 to 1:1.2, and more preferably from about 1:0.5 to about 1:1.1.

In the conditioners of the invention, the level of cationic surfactant is preferably from 0.01 to 10, more preferably 0.05 to 5, most preferably 0.1 to 4 percent by weight of the total composition.

Fatty Materials

Conditioner compositions of the invention preferably additionally comprise fatty materials. The combined use of fatty materials and cationic surfactants in conditioning compositions is believed to be especially advantageous, because this leads to the formation of a structured lamellar or liquid crystal phase, in which the cationic surfactant is dispersed.

By "fatty material" is meant a fatty alcohol, an alkoxylated fatty alcohol, a fatty acid or a mixture thereof. Preferably, the alkyl chain of the fatty material is fully saturated.

Representative fatty materials comprise from 8 to 22 carbon atoms, more preferably 16 to 22. Examples of suitable fatty alcohols include cetyl alcohol, stearyl alcohol and mixtures thereof. The use of these materials is also advantageous in that they contribute to the overall conditioning properties of compositions of the invention.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof.

The level of fatty material in conditioners of the invention is suitably from 0.01 to 15, preferably from 0.1 to 10, and more preferably from 0.5 to 4 percent by weight of the total composition. The weight ratio of cationic surfactant to fatty alcohol is suitably from 10:1 to 1:10, preferably from 4:1 to 1:8, optimally from 1:1 to 1:7, for example 1:3.

Adjuvants

The compositions of the present invention may also contain adjuvants suitable for hair care. Generally such ingredients are included individually at a level of up to 2%, preferably up to 1% by weight of the total composition.

Among suitable hair care adjuvants, are natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts. A particularly preferred combination of natural hair root nutrients for inclusion in compositions of the invention is isoleucine and glucose. A particularly preferred amino acid nutrient is arginine. Another suitable adjuvant is glycolic acid.

Optional Ingredients

Compositions of this invention may contain any other ingredient normally used in hair treatment formulations. These other ingredients may include viscosity modifiers, preservatives, colouring agents, polyols such as glycerine and polypropylene glycol, chelating agents such as EDTA, antioxidants, fragrances, antimicrobials and sunscreens. Each of these ingredients will be present in an amount effective to accomplish its purpose. Generally these optional ingredients are included individually at a level of up to 5% by weight of the total composition.

Preparation of Compositions

One method for preparing compositions according to the invention is to add hydrophobic conditioning oil to the other components comprising the hair conditioner composition, followed by suitable mixing of the composition in order to ensure that the blend is dispersed as droplets of a suitable size.

However it is preferred if the hydrophobic conditioning oil is first formed into an aqueous emulsion prior to incorporation into the hair conditioner composition. Thus another aspect of the invention is a method for preparing an aqueous hair conditioner composition comprising the steps of:
i) preparing a solution comprising water and the surface active block copolymer,.
ii) adding a water-insoluble conditioning oil to the solution,
iii) forming the solution and the conditioning oil into an oil-in-water emulsion by high-shear mixing,
iv) dispersing the oil-in-water emulsion comprising the block copolymer into a hair conditioner composition.

Another preferred method for preparing a hair conditioning composition according to the invention comprises the steps of:
i) preparing an oil-in-water emulsion of a water-insoluble conditioning oil,
ii) dispersing the surface active block copolymer into the emulsion,
iii) dispersing said oil-in-water emulsion comprising the block copolymer into a hair conditioner composition.

Suitable emulsifiers for use in the preparation of the aqueous emulsion are well known in the art and include anionic, cationic, zwitterionic, amphoteric and nonionic surfactants, and mixtures thereof. Examples of anionic surfactants used as emulsifiers for the conditioning oil particles are alkylarylsulphonates, e.g., sodium dodecylbenzene sulphonate, alkyl sulphates e.g., sodium lauryl sulphate, alkyl ether sulphates, e.g., sodium lauryl ether sulphate nEO, where n is from 1 to 20, alkylphenol ether sulphates, e.g., octylphenol ether sulphate nEO where n is from 1 to 20, and sulphosuccinates, e.g., sodium dioctylsulphosuccinate.

Examples of nonionic surfactants suitable for use as emulsifiers for the conditioning oil droplets are alkylphenol ethoxylates, e.g., nonylphenol ethoxylate nEO, where n is from 1 to 50 and alcohol ethoxylates, e.g., lauryl alcohol nEO, where n is from 1 to 50, ester ethoxylates, e.g., polyoxyethylene monostearate where the number of oxyethylene units is from 1 to 30.

A preferred process for preparing oil-in-water emulsions of the droplets comprising the hydrophobic conditioning oil, which can then be incorporated in the hair treatment compositions, involves use of a mixer. Depending upon the viscosity of the conditioning oil, a suitable mixer should be chosen so as to provide sufficient shear to give the required final particle size of the emulsion. Examples of suitable benchtop mixers spanning the range of necessary shear are Heidolph RZR2100, Silverson L4R, Rannie mini-lab high pressure homogeniser and Ystral X10/20-750. Other mixers of similar specification are well known to those skilled in the art and can also be used in this application. Equally it is possible to manufacture oil-in-water emulsions of this description on larger scale mixers which offer similar shear regimes to those described above.

It is also possible to produce suitable emulsions, for use in compositions according to the invention, by means of emulsion polymerisation of the silicone rather than by mechanical emulsification. In this case a preferred process is to add the block copolymer to the emulsion after emulsion polymerisation before combining the blend of emulsion and block copolymer with the rest of the composition. Preferably, the mixer is also capable of controlling the temperature of the components during mixing, e.g. it comprises a jacket through which a heat transfer fluid can be circulated.

It is preferred if the aqueous phase of the emulsion contains a polymeric thickening agent to prevent phase separation of the emulsion after preparation. Preferred thickening agents are cross-linked polyacrylates, cellulosic polymers or derivatives of cellulosic polymers.

Mousses

Hair conditioner compositions in accordance with the invention may also take the form of aerosol foams (mousses) in which case a propellant may be included in the composition. This agent is responsible for expelling the other materials from the container and forming the hair mousse character.

The propellant gas can be any liquefiable gas conventionally used for aerosol containers. Examples of suitable propellants include dimethyl ether, propane, n-butane and isobutane, used singly or in admixture.

The amount of the propellant gases is governed by normal factors well known in the aerosol art. For hair mousses, the level of propellant is generally from 3 to 30, preferably from 5 to 15% by weight of the total composition.

Alternatively, the mousse may be generated mechanically without the need for a propellant by use of a suitable foam-generating container.

Mode of Use

The compositions of the invention are primarily intended for topical application to the hair and/or scalp and or skin of a human subject as rinse-off treatments to improve hair fibre surface properties such as smoothness, softness, manageability, cuticle integrity, and shine. In particular, compositions according to the invention are used for improving the deposition of conditioning oil onto the tip region of hair.

Thus another aspect of the invention is a method for enhancing deposition of water-insoluble conditioning oil from a hair-conditioner composition onto the hair tip region by applying to the hair a composition according to the invention followed by rinsing with water.

A further aspect of the invention is the use of a composition according to the invention for enhancing deposition of water-insoluble conditioning oil onto the tip region of hair.

The invention is further demonstrated with reference to the following, non-limiting examples:

EXAMPLES

Various hair conditioner compositions were prepared using as a basis the formulation in table 1.

TABLE 1

| Chemical Name | Tradename | Weight % (as 100% active) |
|---|---|---|
| Behenyl trimethylammonium chloride | Genamin KDMP (85% active) | 2.0 |
| Cetearyl Alcohol | Laurex | 4.0 |
| Preservative | Nipagen M | 0.2 |
| Silicone | DC1785 | 3.0 |
| Polaxamer | Pluronic (see table 2) | 0.09 |
| Water | — | to 100 |

Examples 1 to 9 and B, C and D were made up using the relevant Polaxamer as detailed in table 2. Example A was made up without Polaxamer present.

Examples A to D are comparative examples outside the scope of the invention whereas examples 1 to 9 are according to the invention.

Test Method 0.25g/5 cm switches of tip hair which had been cleaned with a solution of 14% SLES 2EO and 2% cocoamidopropyl betaine in water followed by extensive rinsing, were used for this experiment. The test hair conditioner composition was diluted to 1 in 5 by weight with distilled water and stirred throughout with a magnetic stirrer. 5 switches were placed in one half of a petri dish. 1.5 mls of diluted hair conditioner was placed along the length of the switches which were then agitated in the dish for 30 seconds, followed by a rinse for 30 seconds under tap water (12° French hard) at 40° C., with a flow rate set at 3-4 liters per minute. The switches were then allowed to dry naturally at 25° C. and a relative humidity of 45 to 60%.

A control experiment was carried out without use of the conditioner, to obtain the background level of silicone present on the tip hair switches.

The amount of silicone deposited on the hair samples was measured using X-ray fluorescence spectrometry (measured in parts per million (ppm) of silicon).

Analysis Results

The tip deposition was calculated as (ppm silicon for test sample—ppm silicon for control experiment).

TABLE 2

| Example | Polaxamer or Tetronic Name | x | y | x/y | Tip Deposition (Silicon ppm) |
|---|---|---|---|---|---|
| 1 | L44 | 10 | 21 | 0.48 | 344 |
| 2 | L64 | 13 | 30 | 0.43 | 342 |
| 3 | P84 | 19 | 39 | 0.49 | 279 |
| 4 | F77 | 52 | 35 | 1.49 | 310 |
| 5 | F87 | 61 | 39 | 1.56 | 286 |
| 6 | F68 | 76 | 30 | 2.53 | 386 |
| 7 | F88 | 103 | 39 | 2.64 | 549 |
| 8 | F98 | 123 | 47 | 2.62 | 259 |
| 9 | F108 | 132 | 56 | 2.36 | 394 |
| 10 | T908 | — | — | — | 263 |
| 11 | T1307 | — | — | — | 365 |
| A | — | — | — | — | 236 |
| B | L31 | 1 | 16 | 0.06 | 202 |
| C | P103 | 17 | 56 | 0.30 | 182 |
| D | F127 | 99 | 69 | 1.43 | 134 |
| E | F38 | 42 | 16 | 2.63 | 222 |

The invention claimed is:

1. An aqueous hair conditioner composition comprising:
   a) a cationic conditioning surfactant,
   b) discrete, dispersed droplets comprising a water-insoluble conditioning oil comprising silicone oil,
   c) a block copolymer with a mean molecular weight of 1000 unified atomic mass units or more, comprising polyethyleneoxide and polypropyleneoxide blocks selected from the group consisting of (i) poloxamers according to formula I:

I:

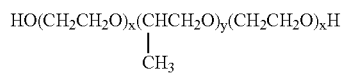

wherein the mean value of y is from 18 to 60 and the mean value x is from 7 to 140 such that the mean value of the ratio x/y is from 0.4 to 3.0
and (ii) poloxamines according to formula II:

II:

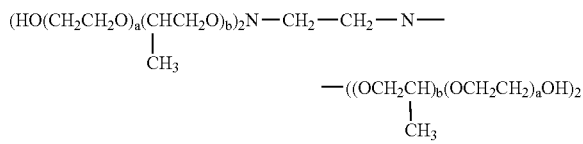

wherein the mean value of a is 2 or more and the mean value of b is 2 or more, and
   d) from 0.01 to 15% by weight of a fatty material selected from the group consisting of fatty alcohols, ethoxylated fatty alcohols, fatty acids and mixtures thereof;
and wherein:
   the cationic conditioning surfactant is present in the aqueous hair conditioner composition in an amount of 0.05 to 5% by weight;
   the water insoluble conditioning oil is present in the aqueous hair conditioner composition in an amount of 0.2 to 6% by weight and comprises silicone oil; and
   the block copolymer is present in the aqueous hair conditioner composition in an amount of from 0.01 to 0.7% by weight of the composition; and
wherein the water-insoluble conditioning oil is dispersed into the aqueous hair conditioner composition as an oil-in-water emulsion formed by a process comprising steps of:
   i) preparing a solution comprising water and the block copolymer,
   ii) adding the water-insoluble conditioning oil to the solution, and
   iii) forming the solution and the conditioning oil into the oil-in-water emulsion by high shear mixing; and
wherein the aqueous hair conditioner composition is itself an oil-in-water emulsion.

2. An aqueous hair conditioner composition comprising:
   a) a cationic conditioning surfactant,
   b) discrete, dispersed droplets comprising a water-insoluble conditioning oil comprising a silicone oil comprising silicone oil,
   c) a block copolymer with a mean molecular weight of 1000 unified atomic mass units or more, comprising polyethyleneoxide and polypropyleneoxide blocks selected from the group consisting of (i) poloxamers according to formula I:

I:

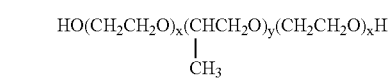

wherein the mean value of y is from 18 to 60 and the mean value x is from 7 to 140 such that the mean value of the ratio x/y is from 0.4 to 3.0
and (ii) poloxamines according to formula II:

II:

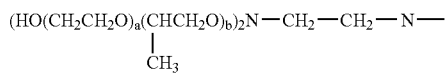

-continued

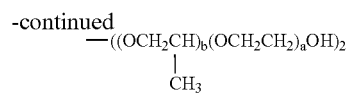

wherein the mean value of a is 2 or more and the mean value of b is 2 or more, d) from 0.01 to 15% by weight of a fatty material selected from the group consisting of fatty alcohols, ethoxylated fatty alcohols, fatty acids and mixtures thereof;

wherein:
the cationic conditioning surfactant is present in the aqueous hair conditioner composition in amount of 0.05 to 5% by weight;
the water insoluble conditioning oil is present In the aqueous hair conditioner composition in an amount of from 0.2 to 6% by weight; and
the block copolymer is present in the aqueous hair conditioner composition in an amount of from 0.01 to 0.7% by weight; and
wherein the water-insoluble conditioning oil is dispersed into the aqueous hair conditioner composition as a emulsion formed by a process comprising the steps of:
  i) preparing, by means of emulsion polymerization, an oil-in-water emulsion of the water-insoluble conditioning oil, and
  ii) dispersing the block copolymer in the emulsion; and
wherein the aqueous hair conditioner composition is itself an aqueous oil-in-water emulsion.

3. An aqueous hair conditioner composition according to claim 1 that is a rinse-off product.

4. An aqueous hair conditioner composition according to claim 1 that is in the form of a rinse-off or leave-on mousse.

5. An aqueous hair conditioner composition according to claim 1 wherein the cationic conditioning surfactant is according to formula III:

$$[N(R_1)(R_2)(R_3)(R_4)]^+(X)^-$$

wherein $R_1, R_2, R_3,$ and $R_4$ are independently selected from (a) an aliphatic group of from 1 to 22 carbon atoms, or (b) an aromatic, alkoxy, polyoxyalkylene, alkylamido, hydroxyalkyl, alkoylalkyl, aryl or alkylaryl group having up to 22 carbon atoms; and X is a salt-forming anion.

6. An aqueous hair conditioner composition according to claim 1 wherein the composition comprises from 0.1% to 0.4% by weight of the block copolymer.

7. An aqueous hair conditioner composition according to claim 1 wherein the composition comprises from 0.1% to 4% by weight of the cationic conditioning surfactant.

8. An aqueous hair conditioner composition according to claim 1 wherein the composition comprises from 0.5% to 4% by weight of water-insoluble conditioning oil.

9. An aqueous hair conditioner composition according to claim 1 wherein the water-insoluble conditioning oil is a silicone conditioning oil.

10. An aqueous hair conditioner composition according to claim 2 wherein the cationic conditioning surfactant is according to formula III:

$$[N(R_1)(R_2)(R_3)(R_4)]^+(X)^-$$

wherein $R_1, R_2, R_3,$ and $R_4$ are independently selected from (a) an aliphatic group of from 1 to 22 carbon atoms, or (b) an aromatic, alkoxy, polyoxyalkylene, alkylamido, hydroxyalkyl, alkoylalkyl, aryl or alkylaryl group having up to 22 carbon atoms; and X is a salt-forming anion.

11. An aqueous hair conditioner composition according to claim 9 wherein the composition comprises from 0.1 to 10% by weight of fatty material and wherein the weight ratio of cationic surfactant to fatty material is from 1:1 to 1:7.

12. An aqueous hair conditioner composition according to claim 1 wherein the block copolymer is present in the composition in an amount of from about 0.01% to 0.4% by weight and the water-insoluble conditioning oil is present in the composition in an amount of from 0.5% to 4% by weight.

13. An aqueous hair conditioner composition according to claim 2 wherein the block copolymer is present in the composition in an amount of from about 0.01% to 0.4% by weight and the water-insoluble conditioning oil is present in the composition in an amount of from 0.5% to 4% by weight.

14. An aqueous hair conditioner composition according to claim 1 that is a composition which is applied to the hair after washing or shampooing and subsequent rinsing.

15. An aqueous hair conditioner composition comprising:
  a) a cationic conditioning surfactant,
  b) discrete, dispersed droplets comprising a water-insoluble conditioning oil comprising silicone oil,
  c) a block copolymer with a mean molecular weight of 1000 unified atomic mass units or more, comprising polyethyleneoxide and polypropyleneoxide blocks selected from the group consisting of (i) poloxamers according to formula I:

I:

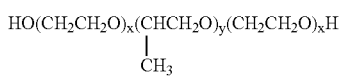

wherein the mean value of y is from 18 to 60 and the mean value x is from 7 to 140 such that the mean value of the ratio x/y is from 0.4 to 3.0
and (ii) poloxamines according to formula II:

II:

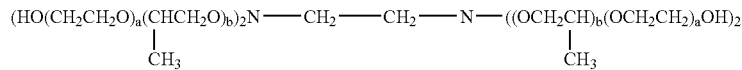

wherein the mean value of a is 2 or more and the mean value of b is 2 or more, and d) from 0.01 to 15% by weight of a fatty material selected from the group consisting of fatty alcohols, ethoxylated fatty alcohols, fatty acids and mixtures thereof;

and wherein:
the aqueous hair conditioner composition is an oil-in-water emulsion;

the cationic conditioning surfactant is present in the aqueous hair conditioner composition in an amount of 0.05 to 5% by weight;

the water insoluble conditioning oil is present in the aqueous hair conditioner composition in an amount of 0.2 to 6% by weight; and the block copolymer is present in the aqueous hair conditioner composition in an amount of from 0.01 to 0.7% by weight of the composition.

* * * * *